(12) United States Patent
Hansen et al.

(10) Patent No.: US 7,615,155 B1
(45) Date of Patent: Nov. 10, 2009

(54) METHODS FOR REMOVAL OF NON-DIGESTIBLE MATTER FROM AN UPFLOW ANAEROBIC DIGESTER

(75) Inventors: Conly L. Hansen, North Logan, UT (US); Carl S. Hansen, Garland, UT (US); Edward D. Watts, North Logan, UT (US); Kevin D. Pack, North Logan, UT (US); Jacob Shaun Dustin, Logan, UT (US)

(73) Assignee: Utah State University, Logan, UT (US)

( * ) Notice: Subject to any disclaimer, the term of this patent is extended or adjusted under 35 U.S.C. 154(b) by 0 days.

(21) Appl. No.: 12/185,692

(22) Filed: Aug. 4, 2008

(51) Int. Cl.
*C02F 11/04* (2006.01)
*C02F 3/28* (2006.01)

(52) U.S. Cl. ...................... 210/603; 210/616
(58) Field of Classification Search ................ 210/603, 210/608, 614, 615, 616, 617, 629
See application file for complete search history.

(56) References Cited

U.S. PATENT DOCUMENTS

| | | | | |
|---|---|---|---|---|
| 2,889,929 A | * | 6/1959 | Kivell | 210/194 |
| 4,208,279 A | * | 6/1980 | Varani | 210/613 |
| 4,302,329 A | * | 11/1981 | Pfefferkorn | 210/97 |
| 4,350,588 A | * | 9/1982 | Tsubota | 210/208 |
| 6,063,273 A | * | 5/2000 | Habets et al. | 210/188 |
| 6,592,751 B2 | * | 7/2003 | Haridas | 210/97 |
| 6,911,149 B2 | * | 6/2005 | Hansen et al. | 210/603 |
| 7,290,669 B1 | * | 11/2007 | Hansen et al. | 210/525 |
| 7,452,467 B2 | * | 11/2008 | Hansen et al. | 210/603 |

* cited by examiner

Primary Examiner—Fred Prince

(57) ABSTRACT

Methods for steady state operation of an upflow anaerobic digester using organic matter that contains a portion of solid, non-digestible matter include (1) providing an upflow anaerobic digester, (2) providing a bacterial culture in the upflow anaerobic digester for the breakdown of organic matter, (3) introducing an influent into the upflow anaerobic digester, wherein the influent comprises a biodegradable component, a liquid component, and an amount of solid non-digestible matter, (4) operating the upflow anaerobic digester in a steady-state, (5) accumulating the solid, non-digestible matter in the upflow anaerobic digester, (6) and removing a portion of the accumulated solid, non-digestible matter from the upflow anaerobic digester through the bottom of the upflow anaerobic digester while maintaining steady-state operation of the upflow anaerobic digester. Steady-state operation of the upflow anaerobic digester is maintained by selecting a percentage of the total volume of the liquid and material that are flushed from the digester for a given period of time so as to preserve the steady-state of the bacterial culture.

28 Claims, 9 Drawing Sheets

METHODS FOR REMOVAL OF NON-DIGESTIBLE MATTER FROM AN UPFLOW ANAEROBIC DIGESTER

CROSS-REFERENCE TO RELATED APPLICATIONS

U.S. Pat. No. 6,911,149 entitled "INDUCED SLUDGE BED ANAEROBIC REACTOR," U.S. Pat. No. 7,290,669 entitled "UPFLOW BIOREACTOR HAVING A SEPTUM AND AN AUGER AND DRIVE ASSEMBLY," and U.S. patent application Ser. No. 11/272,293, filed Nov. 10, 2005, now U.S. Pat. No. 7,452,467 entitled "INDUCED SLUDGE BED ANAEROBIC REACTOR" are hereby incorporated by reference in their entirety.

BACKGROUND OF THE INVENTION

1. The Field of the Invention

The present invention relates to upflow bioreactors for digesting biodegradable materials. More particularly, the present invention relates to methods for digesting biodegradable materials that contain an amount of solid, non-digestible matter.

2. The Relevant Technology

A bioreactor is a device that uses bacteria to promote the decomposition, biodegradation, or "digestion" of organic waste materials into simple organics and gaseous biogas products. Biogas is typically a mixture of methane, carbon dioxide, hydrogen sulfide, and other volatile organic compounds. If produced in sufficient quantities, the methane gas can be used as a fuel. A bioreactor can also be used to treat and detoxify organic waste matter and wastewater.

Anaerobic digestion is a traditional method used to treat wastewater containing high concentrations of organic matter. Anaerobic digestion removes large quantities of organic matter from the waste material and produces biogas as a useful byproduct. Anaerobic digestion is particularly suitable for wastewater containing high concentrations of organics, such as wastewater generated through agricultural production and processing.

Many attempts have been made to decompose organic waste using closed vessels. One type of closed vessel reactor that has shown high decomposition rates is the upflow anaerobic sludge blanket reactor. In this reactor, waste material is introduced into the bottom of the reactor and forced up through the vessel where it passes through a blanket of bacteria, which decompose the organic material to produce biogas that can be collected and used as a fuel.

To achieve high decomposition rates in an upflow bioreactor, the bacterial culture should be well established. Establishing the bacterial culture can be time consuming. It typically requires up to six-months to start up a new reactor and establish the bacterial culture. Nevertheless, one important advantage of an upflow bioreactor is that it can be operated continuously. Thus, once the bacterial culture is established, the high rate of digestion can be maintained for an extended period of time (e.g. months or even years).

Such continuous operation is, however, problematic in situations where the waste stream contains a high proportion of non-digestible inorganic matter, such as sand and organic matter that is not readily digested, such as hair or sawdust. The materials tend to collect in the in the digester over time and reduce the efficiency of the digester.

BRIEF SUMMARY OF THE INVENTION

The present invention relates to methods and apparatuses for continuous, steady-state operation of upflow anaerobic reactor, which is also referred to herein as a digester or a bioreactor (these terms are used synonymously) for digesting biodegradable matter that contains solid, non-digestible matter. The upflow anaerobic reactor contains a population of bacteria that become established in the reactor vessel (typically over a relatively long period of time) and, once established, the bacteria are capable of growing and consuming the biodegradable matter in a steady-state.

The upflow anaerobic reactor includes a septum that helps establish and maintain the bacterial culture. The septum has an aperture that allows fluids to flow up and out of the bioreactor. In operation, at least a portion of the solids that are traveling up through the reactor collide with the underside of the septum and settle back into the thick culture of bacteria in the bottom portion of the bioreactor while some digested solids flow out of the reactor. The septum is very effective at retaining solids in the digester compared to upflow bioreactor without a septum. As the biodegradable matter is consumed solid, non-digestible matter tends to accumulate at the bottom of the bioreactor vessel.

The devices and methods of the present invention allow for removal of the accumulated solid, non-digestible matter without also removing or overly disturbing the established bacterial population, so as to continue operating the bioreactor in a steady-state. A digester operating at steady-state has bacterial population that is relatively stable. The bacterial population is primarily composed of desirable bacteria that rapidly decompose the biodegradable matter, yielding large quantities of biogas. The waste material that is introduced into the bioreactor includes bacteria that are undesirable because they do not perform these tasks optimally. However, in steady-state operation of the digester, the established desirable bacteria out-compete the undesirable bacteria, thereby preserving efficient operation of the bioreactor.

The devices and methods of the present invention facilitate steady-state operation of an upflow anaerobic digester by removing solid, non-digestible matter in a way that does not significantly disturb the steady state balance in the digester. The removal of solid, non-digestible matter typically results in an unavoidable removal of some of the desirable bacterial culture. The present invention relates to devices and methods that facilitate removal of solid, non-digestible matter in an amount that ensures that the bacterial culture is able to continue to digest the biodegradable matter in the steady state.

The accumulated solid, non-digestible matter is removed from the bottom of the vessel along with a selected percentage of the total volume of liquid within the vessel. Selecting the volume that is removed allows the reactor to continue to operate at a steady-state of bacterial growth and a steady-state of bacterial metabolism. The present invention also includes a method where the intervals between purges to remove solid, non-digestible matter are selected so as to allow sufficient growth of bacteria to maintain steady-state between purges while still removing sufficient solid, non-digestible matter to keep the bioreactor from filling. In one embodiment, purging is carried out at least weekly or more preferably at least daily over an extended period of time (e.g., at least a month).

The methods of the present invention can be carried out in a bioreactor that is capable of creating an upflow wherein an influent is introduced via the lower portion of the vessel and an effluent is withdrawn via the upper portion of the vessel. Preferably, an upflow anaerobic digester includes a vessel having a volume with a top that defines an upper portion of the vessel and a bottom that defines a lower portion of the vessel, a septum positioned within the vessel for maintaining the bacterial culture in the lower portion of the vessel, an aperture formed in the septum for allowing digested biodegradable matter and liquid to flow from the lower portion of the vessel to the upper portion of the vessel, an inlet coupled to the vessel for introducing biodegradable matter into the lower portion of the vessel, a gas port coupled to the upper portion of the vessel for collecting gasses produced in the vessel, a first outlet coupled to the upper portion of the vessel for directing digested biodegradable matter to the outside of the vessel, and a second outlet coupled to the bottom of the vessel for removing accumulated solid, non-digestible matter from the vessel.

Optionally, the upflow anaerobic digester further includes an auger device operatively coupled to the vessel and positioned within the aperture of the septum so as to prevent clogging of the aperture. The auger includes sloping fins to move solids from just above the aperture in the septum downward to some distance beyond the bottom of the aperture toward a lower zone in the bioreactor. Alternatively, the auger can pull solids up through the hole and above the septum where the solids can be removed from the vessel.

In one embodiment, the preset invention includes a method for continuous, steady-state operation of an anaerobic reactor for digesting biodegradable matter containing an amount of solid, non-digestible matter. The method includes steps of (1) providing an upflow anaerobic digester for anaerobically digesting biodegradable matter using a bacterial culture; (2) providing a bacterial culture to form a sludge layer in the lower portion of the vessel; (3) introducing an influent into the lower portion of the vessel, wherein the influent includes a biodegradable component, a liquid component, and an amount of solid non-digestible matter; (4) operating the upflow anaerobic digester in a steady-state, wherein the biodegradable component is continuously available to the bacterial culture as a food source; (5) accumulating the solid, non-digestible matter below the sludge layer in the bottom of the vessel; and (6) removing a portion of the accumulated solid, non-digestible matter from the upflow anaerobic digester through the second outlet as a slurry.

The portion of the accumulated solid, non-digestible matter that is removed as a slurry is selected so as to allow the reactor to continue operating in a steady-state. Preferably the portion of the accumulated solid, non-digestible matter removed as a slurry does not exceed 30% of the volume of the vessel. More preferably, the portion of the accumulated solid, non-digestible matter removed as a slurry does not exceed 20% of the volume of the vessel. Even more preferably, the portion of the accumulated solid, non-digestible matter removed as a slurry does not exceed 10% of the volume of the vessel. Most preferably, the portion of the accumulated solid, non-digestible matter removed as a slurry does not exceed 5% of the volume of the vessel.

In one embodiment, the method of the present invention further includes monitoring the influent to determine the amount of solid non-digestible matter contained in the biodegradable waste matter. For example, the amount of non-combustible matter in the influent may be determined by weighing samples of the influent before and after combustion. The weight of the matter that remains after combustion represents the amount of inorganic matter contained in a sample of influent. Monitoring the influent is useful for determining how often to remove the accumulated solids from the bottom of the vessel.

In one embodiment, the vessel includes a non-planar (i.e., sloped) bottom for facilitating removal of the accumulated non-digestible matter that accumulates at the bottom of the vessel. Opening the outlet at the bottom of a vessel with a sloped bottom allows efficient removal of the accumulated non-digestible matter with minimal liquid removal because of the tendency of the solid to flow toward the opening when the outlet is opened.

In one embodiment, the present invention includes a method for recycling liquid removed from an anaerobic reactor. It is generally the case that liquid is removed from the bio-reactor in the process of purging solid, non-digestible matter. The solids and liquids are flushed into a settling tank where the solids are allowed to settle. Once the liquids and solids have separated, the liquid can be pumped back into the vessel.

In one embodiment of the present invention, the second vessel is a clarifier tank with at least one inlet coupled to the clarifier tank for introducing the flushed solid, non-digestible matter and the liquid into the tank, and at least one outlet for withdrawing liquid from the tank. A suitable example of a clarifier tank is a settling tank in which the flushed solids are allowed to settle out of the liquid. Once the solids have settled, the liquid can be drawn off the top and recycled back into the reactor vessel.

In one embodiment, the bioreactor of the present invention further includes a fluid injection system configured to inject fluid into the accumulated solid, non-digestible matter. Configured as such, the fluid injection system is designed to facilitate removal of the accumulated solid, non-digestible matter.

In one embodiment, the bioreactor of the present invention further includes a sparger assembly situated in the lower portion of the vessel where it is completely below the liquid level. In one embodiment, the sparger assembly is used to fluidize the accumulated solid, non-digestible matter contained in the bottom portion of the vessel by supplying a flow of a liquid to the sparger assembly, and spraying liquid jets from the sparger assembly into the solid, non-digestible matter so as to form a slurry. In one embodiment, the liquid that is supplied to the sparger assembly is liquid effluent that is withdrawn from the upper portion of the vessel. In another embodiment, the liquid that is supplied to the sparger assembly is liquid that is pumped into the vessel.

In one embodiment, the bioreactor of the present invention further includes a plurality of fluid injection ports operably coupled to the vessel. The fluid injection ports are used to inject fluid into the vessel and fluidize the accumulated solid, non-digestible matter so as to form a slurry. In one embodiment, the fluid injection ports are operably anglable so as to allow the flow of liquid to be selectively directed into the accumulated solid, non-digestible matter to facilitate fluidization. In one embodiment, the liquid that is supplied to the fluid injection ports is liquid effluent that is withdrawn from the upper portion of the vessel. In another embodiment, the liquid that is supplied to the fluid injection ports is liquid that is pumped into the vessel.

In one embodiment, the upflow anaerobic digester further includes an auger device operatively coupled to the vessel and positioned within the second outlet so as to facilitate removal of the slurry and prevent clogging of the second outlet. The auger includes sloping fins to move a solid-liquid slurry through the second outlet to prevent the clogging of the outlet. In one embodiment, the auger can be sufficiently long such that it can remove the accumulated solid non-digestible matter and raise it above the liquid level in the digester. This has the advantage that the solids can be removed from the digester with minimal removal of liquid. In an alternative embodiment, the auger can include a mixing apparatus to fluidize the solids and liquid at the bottom of the vessel so as to facilitate removal of the slurry.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The present invention relates to methods and apparatuses for continuous, steady-state operation of upflow anaerobic reactor used for digesting biodegradable matter that contains solid, non-digestible matter. In particular, the present invention relates to methods and apparatuses for digesting waste matter that includes solid, non-digestible matter and that allow for removal of the accumulated solid, non-digestible matter from the bottom portion of the upflow anaerobic reactor while continuing to operate the reactor at a steady-state.

The accumulated solid, non-digestible matter is typically removed from the bottom of the vessel by removing a portion of the accumulated solid, non-digestible matter along with a selected percentage of the total volume of liquid within the vessel. The volume is selected such that the reactor continues to operate at a steady-state of bacterial growth and a steady-state of bacterial metabolism.

II. Upflow Bioreactors

Figure 1:
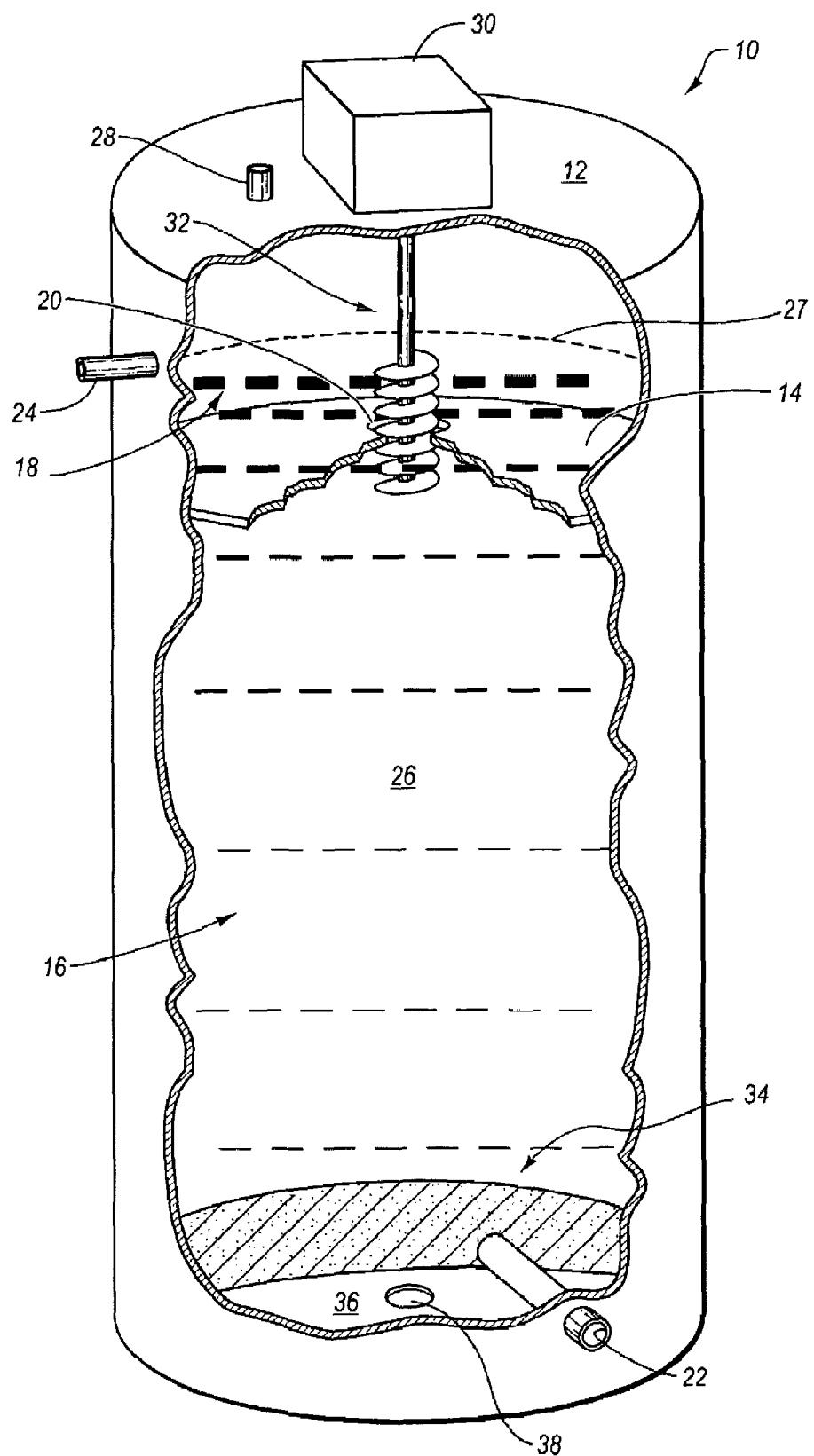
FIG. 1 illustrates an example of an upflow anaerobic digester for digesting organic material that includes a portion of solid, non-digestible matter.

FIG. 1 illustrates an exemplary upflow anaerobic digester 10 according to one embodiment of the present invention. Bioreactor 10 includes a vessel 12 in which biodegradable matter (e.g., sewage or wastewater) can be introduced and held for treatment. A septum 14 is positioned in vessel 12 to form a lower chamber 16 and an upper chamber 18. An aperture 20 in septum 14 provides fluid communication between lower chamber 16 and upper chamber 18. According to one embodiment of the present invention, bioreactor 10 includes an auger 32 to facilitate the retention of solids suspended in the effluent passing through aperture 20 and to prevent the aperture 20 from becoming plugged. A drive assembly 30 generates and/or transfers a force for turning auger 32.

Bioreactor 10 is configured for upflow operation. An inlet 22 is provided in lower chamber 16 for introducing biodegradable matter. A pump (not shown) is typically coupled to inlet 22 to provide pressure for introducing the organic material. An outlet 24 is placed in upper chamber 18 to allow effluent to exit bioreactor 10 near fluid level 27. The placement of inlet 22 in lower chamber 16 and the placement of outlet 24 in upper chamber 18 creates an upflow in bioreactor 10 during operation. The upflow in bioreactor 10 can be operated continuously or semi-continuously by maintaining a continuous or semi-continuous flow of influent into lower chamber 16.

Lower chamber 16 includes a biomass 26 that is within the fluids of the digester. Biomass 26 is also referred to herein as a sludge layer. Biomass 26 includes a microbial culture and biodegradable matter. The upflow in bioreactor 10 is sufficiently slow that a sludge blanket of bacteria can form in the biomass 26 of lower chamber 16. The biodegradable matter (e.g., animal waste and wastewater) is slowly forced up through the sludge blanket where it is decomposed into smaller organic molecules and biogas. The microbial culture present in biomass 26 is selected according to the particular organic material that is to be decomposed in bioreactor 10. In an exemplary embodiment, the microbial culture includes anaerobic bacteria.

In one embodiment, the type of microbial culture and type of organic material are selected such that the decomposition of the organic material produces biogas. Upper chamber 18 can be sealed such that biogas collects within upper chamber 18. A gas outlet 28 allows the biogas to be ported out of bioreactor 10. The biogas can advantageously be used as a fuel. For example, if desired, the biogas can be burned and the heat can be used to maintain an optimal operating temperature in digester 10.

The fluids within vessel 12 have a fluid level 27 that is maintained by effluent outlet 24. The fluid level 27 is set below the top of vessel 12 such that a gas collection chamber is formed between the bioreactor fluids and the top of vessel 12.

Septum 14 is positioned within vessel 12 below fluid level 27. Septum 14 can be rigid or semi-rigid and can be made from any material compatible with the bioreactor fluids, including but not limited to plastics, metals, and the like. Septum 14 can be formed from a plurality of panels, or it can be a single, unitary piece of material. Septum 14 can be secured to the inside of the vessel 12 in any manner.

In one embodiment septum 14 slopes upwardly from the sidewalls of vessel 12 toward aperture 20. Sloping septum 14 can facilitate the removal of materials that settle out in upper chamber 18. A sloped septum can also be advantageous for ensuring that biogas in lower chamber 16 is directed to aperture 20. However, the present invention can also be carried out using a flat septum.

An auger 32 is positioned within aperture 20 of septum 14. Auger 32 can be any device that can be positioned within aperture 20 and can move solids in a desired direction between or within lower and upper chambers 16 and 18. In an exemplary embodiment, the auger includes a shaft with one or more flanges that are configured to move a material in a direction parallel to the shaft.

In one embodiment, auger 32 creates a force that is opposite the flow of fluids in the bioreactor 10. For example, auger 32 can have a flange such that when auger 32 is rotated clockwise, the auger creates a force that is opposite the flow of the bioreactor fluids. During optimal or "normal" operating conditions, auger 32 is rotated in the direction that counters the flow of the bioreactor fluids. This counter-flow force tends to settle out solids suspended in the effluent passing through aperture 20. If aperture 20 becomes clogged, the auger can be rotated in an opposite direction to remove solids to above the septum 14 where the solids can be more easily removed.

Auger 32 and septum 14 are provided to help form and maintain biomass 26. By retaining the bacteria within the lower chamber 16, septum 14 and auger 32 retain more desired bacteria, which are available for breaking down the organic material being fed into digester 10. By utilizing the auger and septum, organic materials can be treated much faster and much more efficiently than organic waste being digested in other bioreactors. In addition, use of the septum and auger improves the clarity of effluent exiting the bioreactor.

Essentially any organic material can be decomposed in digester 10 so long as a microbial culture is available for degrading the organic material and the organic material can be introduced into the bioreactor in a form that can be mixed with the microbes. Examples of suitable organic materials that can be digested in the bioreactors of the present invention include animal wastes produced from the farming, ranching, and agricultural industries, food processing waste, human waste, and the like.

III. Methods for Steady-State Operation of a Bioreactor

In many instances suitable organic material is mixed with materials that are non-digestible and/or not readily digestible in a bioreactor. Examples of materials that are non-digestible and/or not readily digestible in a bioreactor include, but are not limited to, sand, dirt, rocks, sawdust, straw, hair, and the like. For example, cow manure may contain a high proportion of sand if the cows producing the manure have stalls that are bedded with sand.

When manure or other biodegradable organic matter containing a proportion of solid, non-digestible matter is added to an upflow anaerobic digester 10 at least some of the solid, non-digestible matter will settle to the bottom of the reactor. This is shown generally in FIG. 1 at 34. Solid, non-digestible matter 34 can interfere with the bacterial culture in biomass 26. In an extreme case, the accumulated solid, non-digestible matter 34 would eventually fill digester 10 leading to total breakdown of the active digestion of biodegradable matter in the upflow anaerobic digester 10. If this were to occur, digester 10 would have to be shut down, cleaned out, and restarted. This is a particularly unattractive option when considered in light of the amount of time that is required to start up a digester and establish a new bacterial culture (e.g., typically about six-months).

One will of course appreciate, therefore, that it is desirable to develop methods for operating an upflow anaerobic digester 10 whereby accumulated solid, non-digestible matter 34 can be removed periodically from the bottom of digester 10 while continuing operation. At the same time, it is also desirable to allow an operator to remove accumulated solid, non-digestible matter 34 from the vessel 12 without disrupting the sludge layer 26 in the vessel 12 and without overly reducing the volume of material inside the vessel 12 thereby maintaining steady-state operation of digester 10.

It is desirable to avoid reducing the volume of material in the vessel and disruption of the sludge layer because biomass 26 is a complex ecosystem that balances the lifestyles of many different types of bacteria and other microorganisms. When the bacteria and other microorganisms are in balance, they work symbiotically to efficiently breakdown organic matter that is fed into the bioreactor 10. The stages of anaerobic digestion can be broken down into hydrolysis, acidogenesis, and methanogenesis. Specific types of bacteria are required for each stage of the process. In a properly operating anaerobic digester, hydrolyzing bacteria break down large molecules that are then further broken down by acidogens into volatile organic acids (VOA). VOAs are consumed by methanogens, which produce methane as a byproduct.

Once the biomass or sludge layer 26 is established, it is desirable to maintain balance in the digester 10 so that no one type of bacteria outcompetes another type and upsets balance in the vessel 12. This is true at least in part because of the time needed to establish a sludge layer in a typical vessel. For example, it can take up to six-months to establish the many types of bacteria that are needed for the efficient breakdown of the organic matter in an upflow anaerobic digester.

In addition, the organic matter that is introduced into the reactor 10 generally includes bacteria that are different than the bacteria in the sludge layer. For example, animal excrement will include a variety of coliform bacteria, lactobacilli, and yeasts. It is important to maintain the sludge layer such that the bacteria in the sludge layer are able to outcompete the bacteria that are introduced with the organic matter so as to maintain a balanced bacterial population in the sludge layer 26.

Based on the foregoing discussion, one will appreciate, therefore, that one aspect of developing methods for removing accumulated solid, non-digestible matter 34 from digester 10 is removal without disrupting steady state operation of the digester. Maintaining steady-state operation of the digester includes maintaining a balanced and viable bacterial culture in the sludge layer 26.

In one embodiment, the present invention includes a method for continuous, steady-state operation of an anaerobic reactor for digesting biodegradable matter containing an amount of solid, non-digestible matter. In another embodiment, the present invention includes a method for continuous, steady-state production of methane using an upflow anaerobic digester for digesting biodegradable matter containing solid, non-digestible matter. In yet another embodiment, the present invention includes a method for recycling liquid removed from an anaerobic reactor that is used for digesting biodegradable matter containing an amount of solid, non-digestible matter. The methods of the present invention include a common feature in that, accumulated solid, non-digestible matter 34 is removed from the bottom portion of the bioreactor 10 while maintaining steady-state operation. Accumulated solid, non-digestible matter 34 can be removed from the digester as a slurry (i.e. solids and liquids) through a second outlet 38 that is located in or near the bottom surface 36 of the vessel 12. The second outlet 38 will be discussed in greater detail below.

Preferably, the portion of the accumulated solid, non-digestible matter removed as a slurry does not exceed 30% of the volume of the vessel. More preferably, the portion of the accumulated solid, non-digestible matter removed as a slurry does not exceed 20% of the volume of the vessel. Even more preferably, the portion of the accumulated solid, non-digestible matter removed as a slurry does not exceed 10% of the volume of the vessel. Most preferably, the portion of the accumulated solid, non-digestible matter removed as a slurry does not exceed 5% of the volume of the vessel. The volume that is removed is controlled so as to avoid disrupting the bacterial culture in the sludge layer 26 and to avoid reducing the volume of liquid and organic matter in the vessel 12 more than is necessary. Controlling the volume of liquid that is removed from the vessel when removing the solids allows the operator to maintain the upflow anaerobic digester in the steady-state.

In one embodiment of the present invention, the time interval for removal of the accumulated solid, non digestible matter can be determined by monitoring the influent to determine the amount of solid non-digestible matter contained in the organic waste matter. For example, the amount of sand and other non-volatile inorganic matter can be determined by combusting the organic matter and determining the amount of solids left behind. The weight of the solids left after combusting represent the portion of the original that is solid, non-digestible inorganic matter. This amount of solid, non-digestible matter can be drawn out of digester 10 at nearly the same rate that it is introduced into digester 10.

Turning now to FIGS. 2-6, details of several reactor designs are depicted.

Figure 2A:
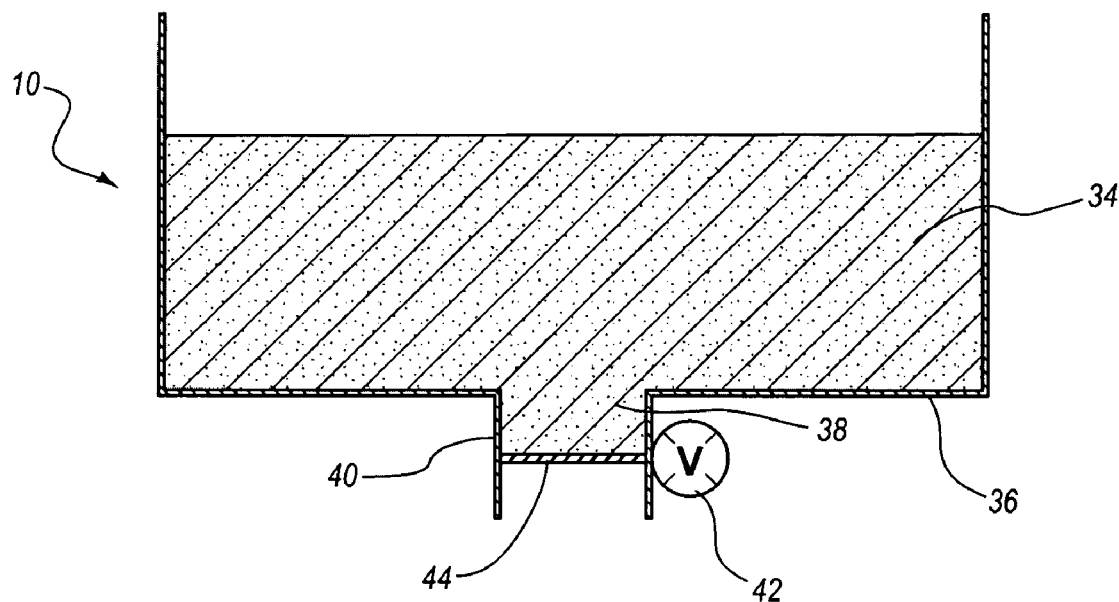
FIG. 2A illustrates the lower portion of a digester showing accumulated solid non-digestible matter.
Figure 2B:
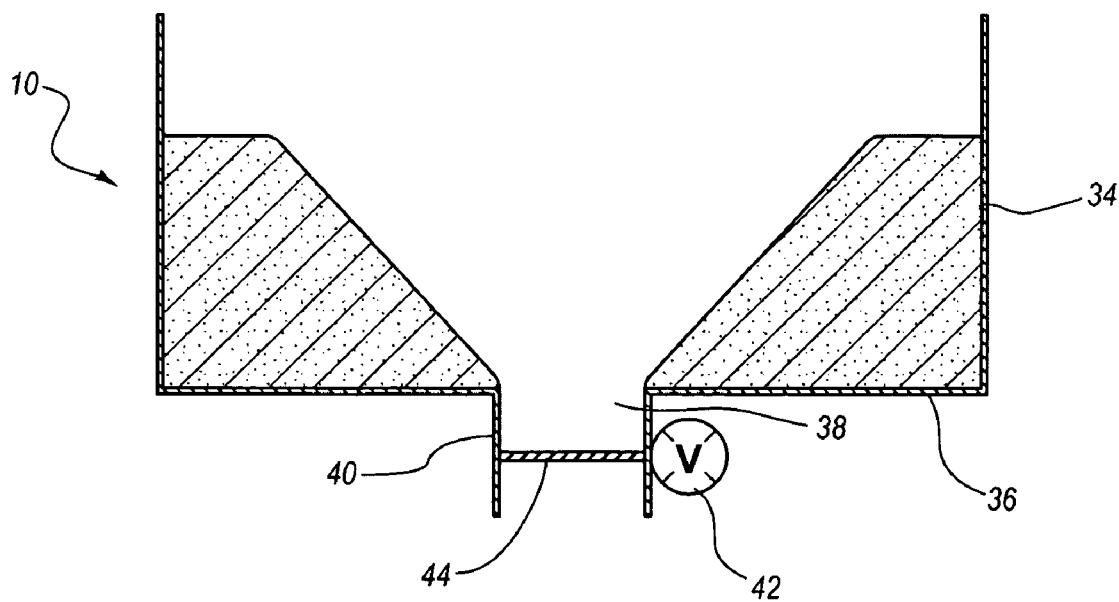
FIG. 2B illustrates the digester of FIG. 2A after a portion of the solid, non-digestible matter has been removed.

FIGS. 2A and 2B depict an embodiment of the present invention wherein the digester 10 has a substantially flat bottom surface 36 and accumulated waste matter 34 is removed using an outlet 38 placed in the bottom 36 of the vessel 12. A layer of accumulated solid, non-digestible matter 34 is removed from the bottom portion of the vessel through the outlet 38. Valve 44 normally maintains the accumulated solid, non-digestible matter 34 and other contents of digester 10 in the vessel 12. Valve 44 may be opened using valve opener 42. Opening valve 44 allows at least a portion of the accumulated solid, non-digestible matter 34 to be flushed from the digester 10 and carried away via a pipe structure 40.

As was explained more fully above, the amount of accumulated matter 34 and accompanying liquid and other solids that are flushed from the digester 10 is selected in order maintain the digester in steady-state operation.

Figure 3A:
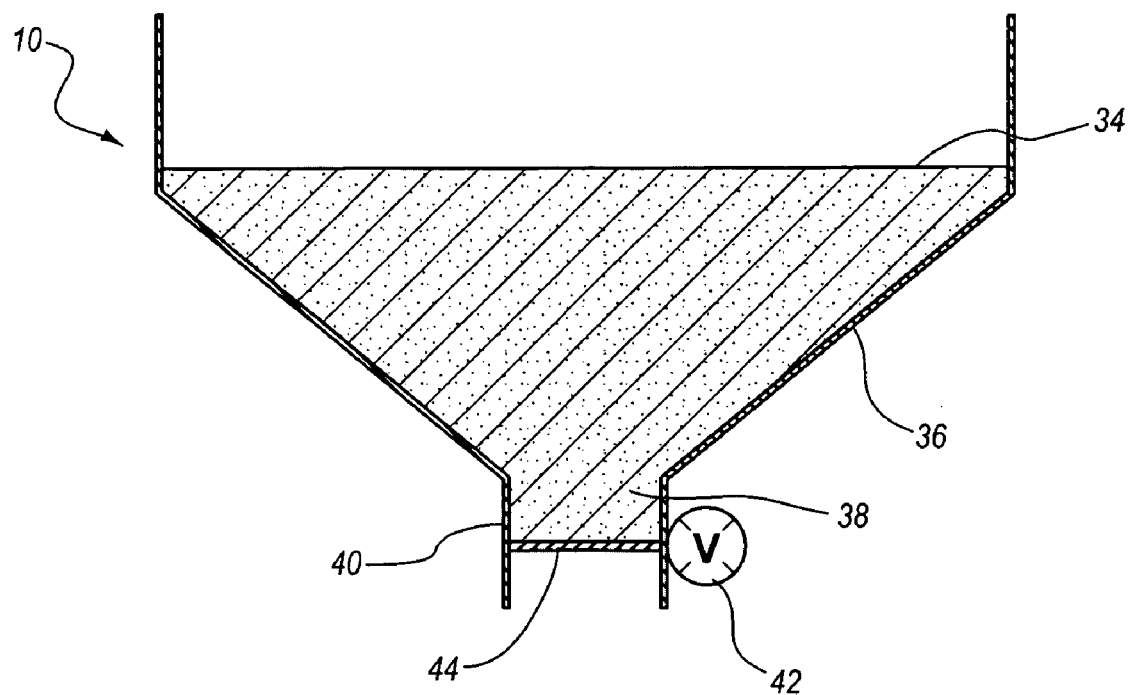
FIG. 3A illustrates the lower portion of a digester showing a digester with a conical bottom and accumulated solid non-digestible matter.
Figure 3B:
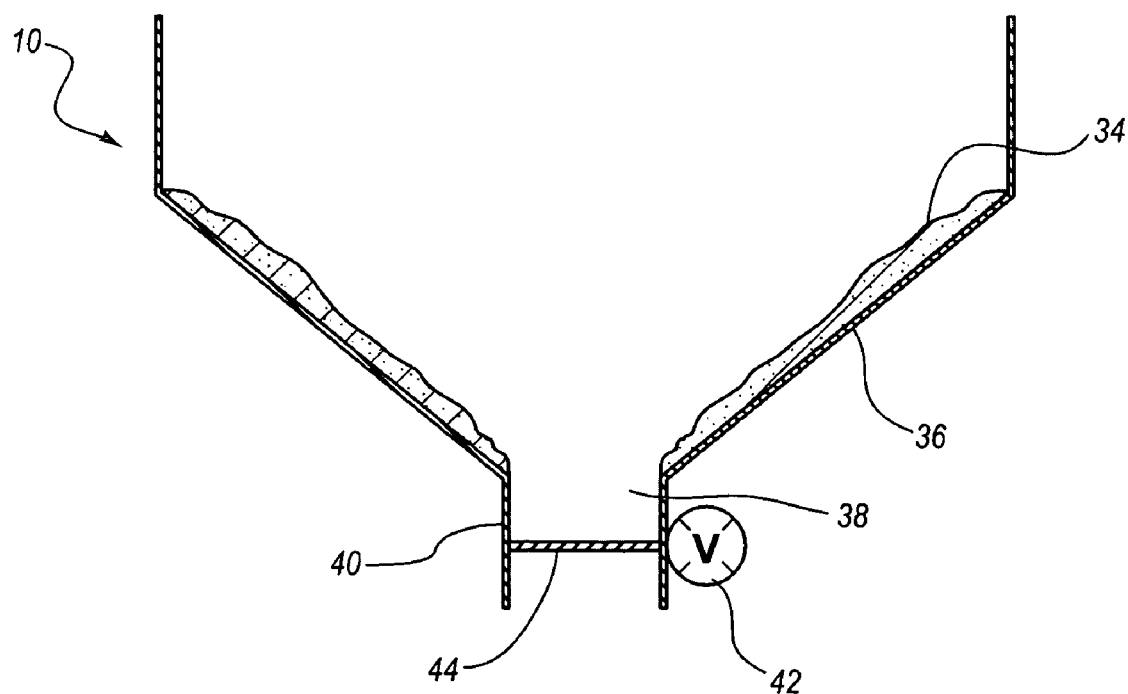
FIG. 3B illustrates the digester of FIG. 3A after a portion of the solid, non-digestible matter has been removed.

FIGS. 3A and 3B depict an alternative embodiment of the present invention wherein digester 10 is equipped with a substantially conical bottom portion 36 for facilitating the removal of the accumulated waste matter 34. The accumulated solid, non-digestible matter is removed as described in regards to FIGS. 2A and 2B. As depicted in FIGS. 3A and 3B, equipping digester 10 with a conical bottom portion 36 allows efficient removal of the accumulated solid non-digestible matter 34. While the conical bottom 36 does facilitate removal of accumulated solid, non-digestible matter, the conical bottom 36 does reduce the overall volume of digester 10, thereby increasing costs compared to a flat-bottom digester having the same volume.

Figure 4A:
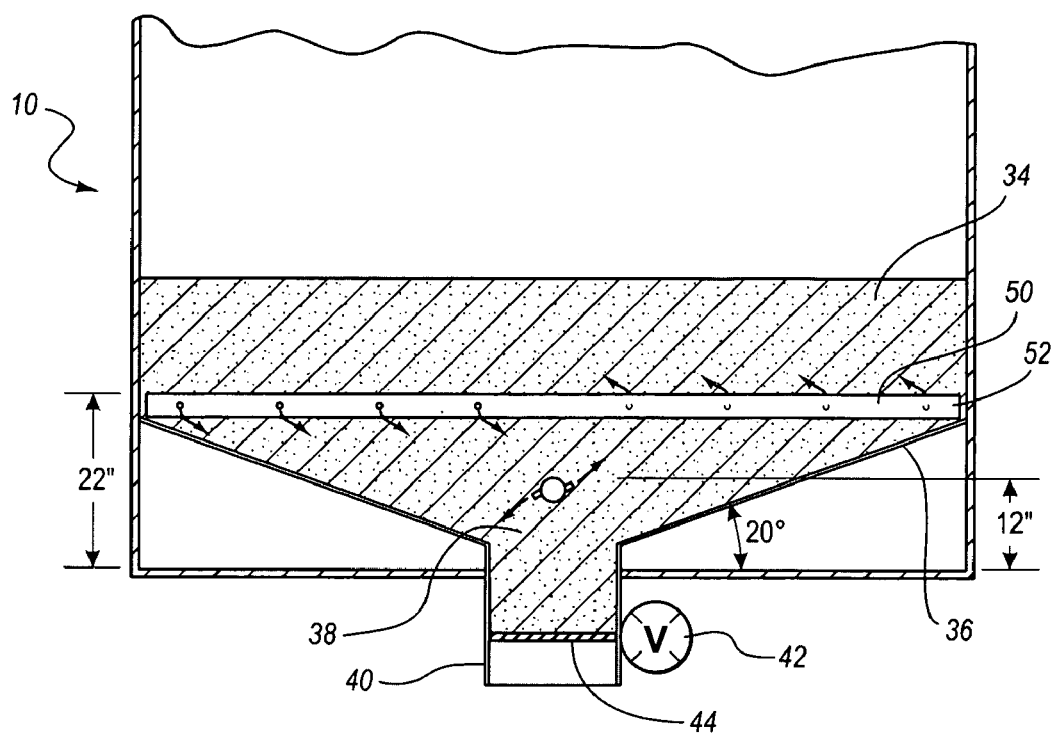
FIG. 4A illustrates the lower portion of a digester showing a digester with a conical bottom, a sparger assembly, and accumulated solid non-digestible matter.
Figure 4B:
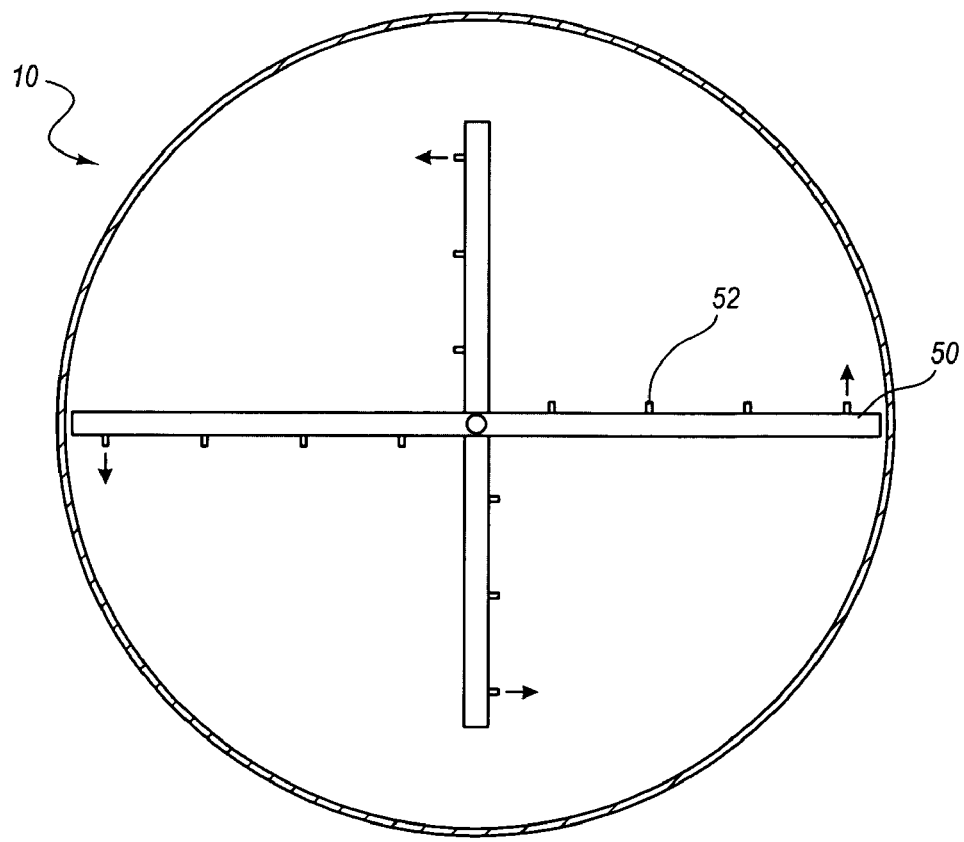
FIG. 4B illustrates a top view of the digester of FIG. 4A.

FIGS. 4A and 4B depict another embodiment of the present invention wherein the digester 10 is equipped with a sparger assembly 50 to facilitate removal of the accumulated matter 34 by ensuring fluidization of the solids. In a preferred embodiment, the sparger assembly 50 is positioned in the lower portion of the digester where it is completely below the level of the fluid in the digester 10. Moreover, the sparger assembly 50 is preferably positioned in the digester such that it is in the region where the solid, non-digestible matter accumulates.

The sparger assembly facilitates removal of the accumulated solid, non-digestible matter 34 by injecting fluid into the layer of solid so as to make a slurry of liquid and solid material. Sparger assembly 50 uses a plurality of liquid nozzles 52 or jets to inject liquid into the layer of accumulated solid, non-digestible matter 34. The nozzles 52 can be directed so as to optimize fluidization of the accumulated matter 34. In one embodiment, the liquid for the sparger assembly 50 is provided by a pump (not shown). The liquid for the sparger assembly can be provided using liquid in the digester 10 such as from the effluent stream, or the liquid can be provided from a source outside the digester 10.

Figure 5A:
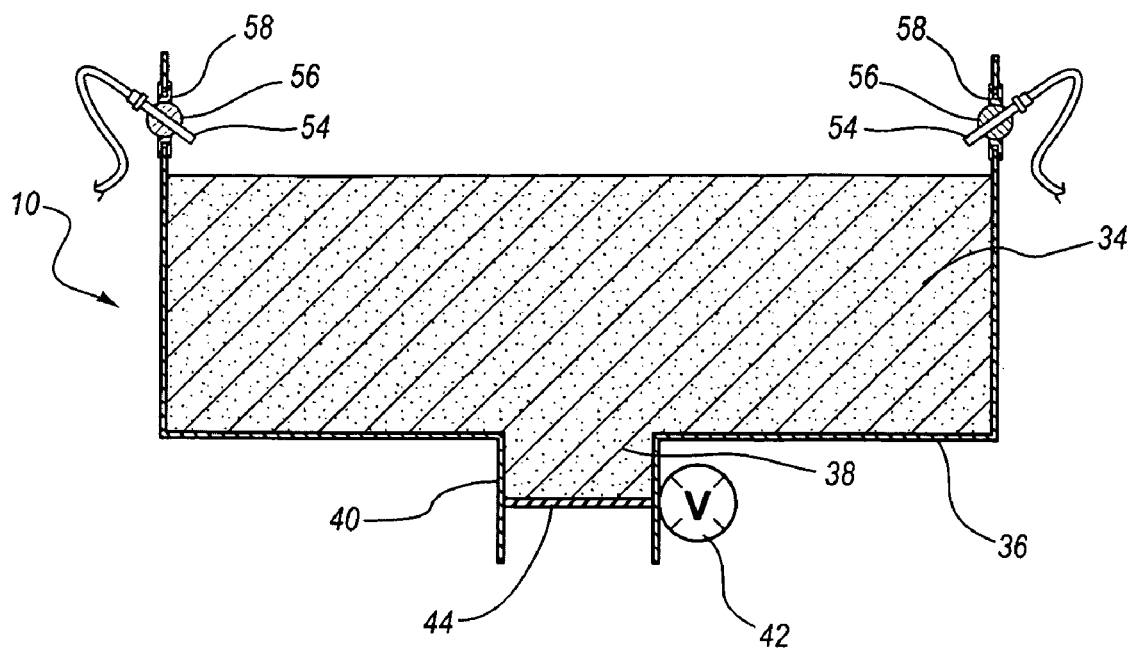
FIG. 5A illustrates the lower portion of a digester showing a digester with a plurality of fluid injection ports and accumulated solid, non-digestible matter.
Figure 5B:
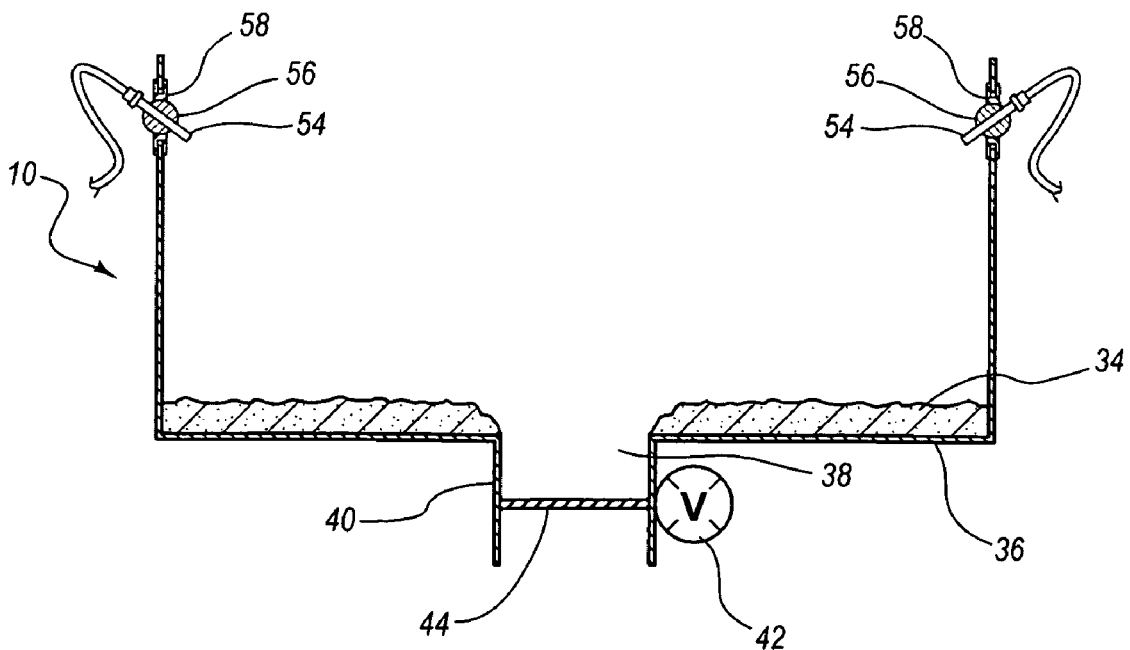
FIG. 5B illustrates the digester of FIG. 5A with the solid, non-digestible matter having been flushed from the digester.

FIGS. 5A and 5B depict another embodiment of the present invention wherein the digester 10 is equipped with a plurality of fluid injection ports 54 to facilitate removal of the accumulated matter 34 by ensuring fluidization of the solids. In a preferred embodiment, plurality of fluid injection ports 54 are positioned in the lower portion of the digester 10. Moreover, the plurality of fluid injection ports 54 are preferably positioned on the digester 10 such that they are in the region where the solid, non-digestible matter 34 accumulates.

The fluid injection ports 54 facilitate removal of the accumulated solid, non-digestible matter 34 by injecting fluid into the layer of solid so as to make a slurry of liquid and solid material. In one embodiment, the fluid injection ports 54 can be directed so as to optimize fluidization of the accumulated matter 34. For example, the fluid injection ports 54 can be attached to the vessel 10 with a ball and socket assembly 56 and 58 that allows for a fluid-tight connection while simultaneously allowing the fluid to be directed into the solid, non-digestible matter for optimal fluidization and solid matter removal. In one embodiment, the liquid for the fluid injection ports is provided by a pump (not shown). The liquid for the fluid injection ports can be provided using liquid in the digester 10 such as from the effluent stream, or the liquid can be provided from a source outside the digester 10.

In one embodiment of the present invention, an auger device is included in or near outlet 38 to facilitate removal of the accumulated solid, non-digestible matter 34 and to prevent clogging of outlet 38 and/or the outlet pipe 48. FIGS. 6A-6H depict a number of exemplary embodiments of digesters 10 that include an auger 60 in or near outlet 38.

Figure 6A:
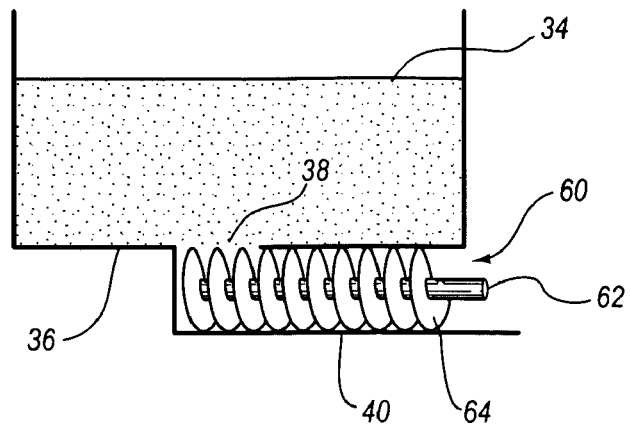
FIG. 6A illustrates a digester that includes an auger assembly in the outlet.

FIG. 6A depicts one embodiment of the present invention wherein an auger assembly 60 is included in outlet pipe 40. Auger assembly 60 includes a shaft 62 and a series of angled flights 64 that are configured to carry accumulated solids 34 away from outlet 38 and down outlet pipe 40.

Figure 6B:
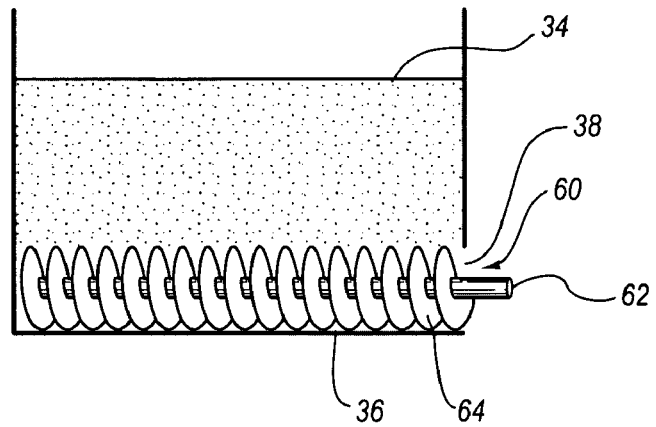
FIG. 6B illustrates a digester that includes an auger assembly that is contained inside the digester.
Figure 6C:
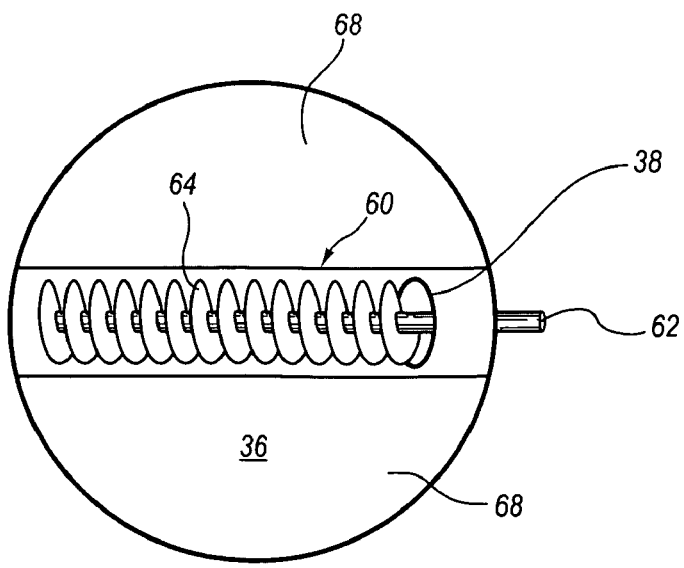
FIG. 6C illustrates an top view of a digester with a trough-shaped bottom and an auger assembly in the trough.
Figure 6D:
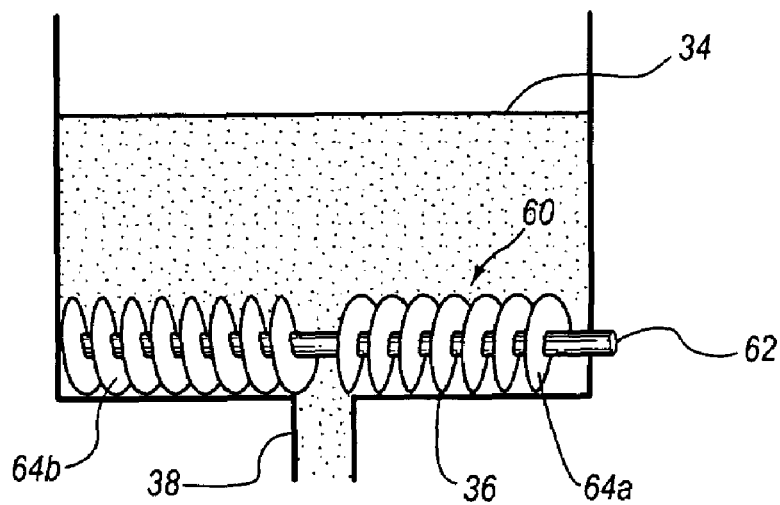
FIG. 6D illustrates a digester that includes an auger assembly that is contained inside the digester wherein the digester has a central outlet and the auger has oppositely oriented flights that feed solid matter to the outlet.

FIGS. 6B-6D depict several related embodiments of the present invention wherein an auger assembly 60 is included inside the vessel 12. The auger assembly 60 depicted in FIGS. 6B-6D is inserted through outlet 38 in the side of digester 10. In the embodiments depicted in FIGS. 6B-6D, auger assembly 60 is rotated by turning shaft 62. Each auger assembly depicted in FIGS. 6B-6D includes a plurality of angled flights that are configured to carry solid material toward outlet 38.

In the embodiment depicted in FIG. 6D, auger assembly 60 is installed in a trough-shaped structure at the bottom of digester 10. The trough is formed by providing digester 10 with sloped sides 68 that form a sloped bottom that feed accumulated solids down to the auger assembly 60. The auger assembly 60 includes angled flights that are configured to carry accumulated solids toward outlet 38.

Figure 6E:
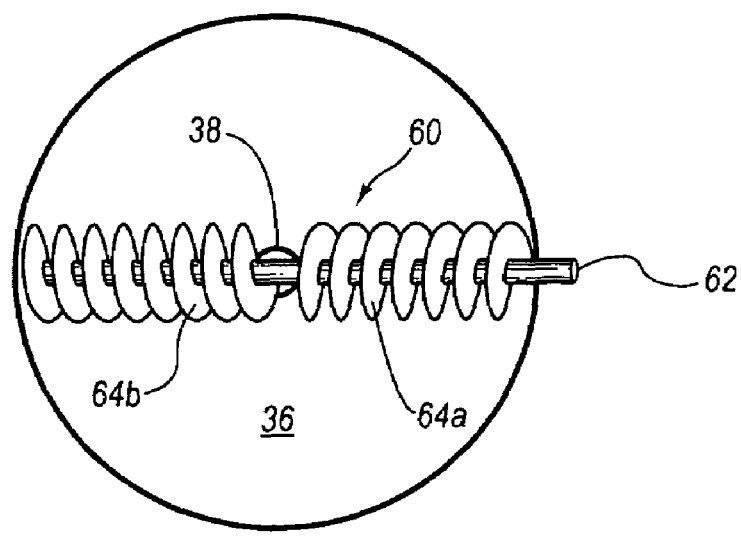
FIG. 6E illustrates a top view of the digester depicted in FIG. 5D.
Figure 6F:
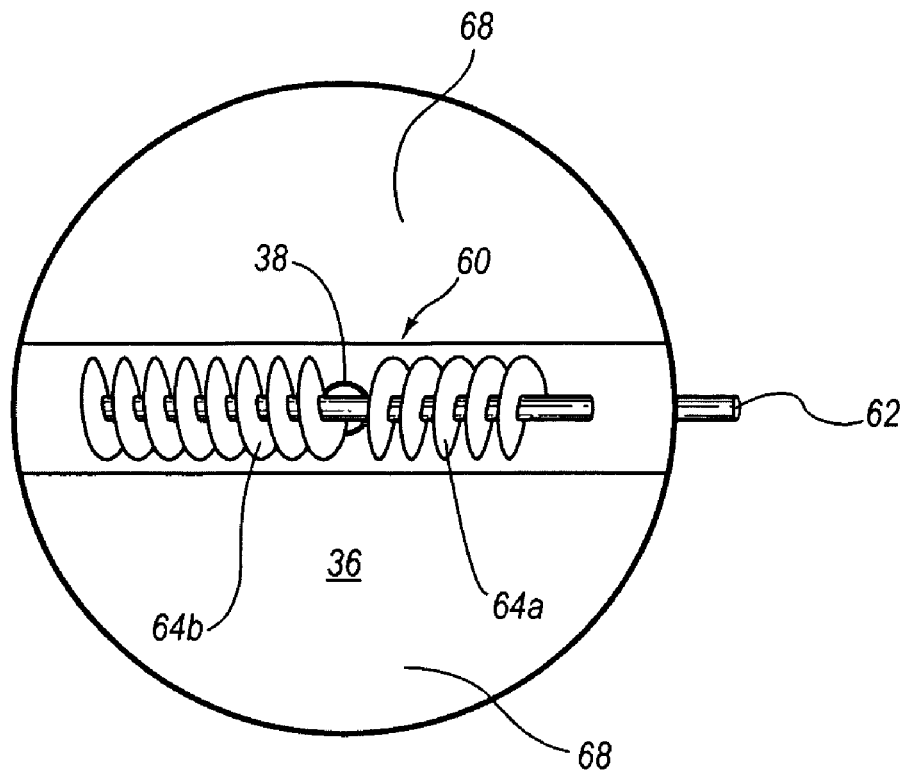
FIG. 6F illustrates a top view of a digester similar to FIG. 5D with the inclusion of a trough.
Figure 6G:
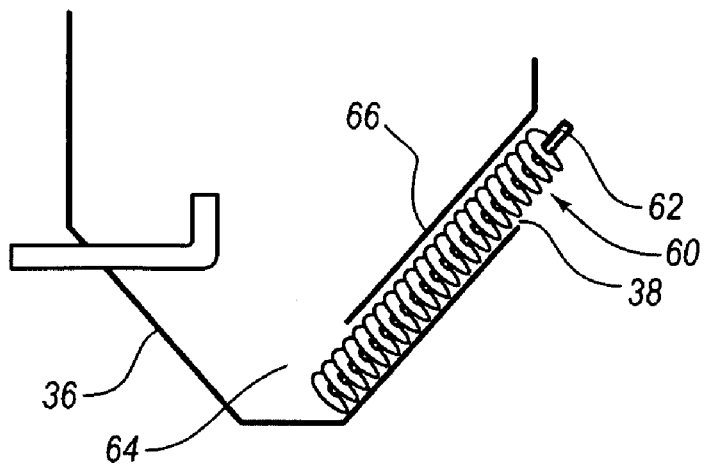
FIG. 6G illustrates a digester that includes a cone-shaped bottom and a auger assembly with flights that are oriented to carry solid non-digestible matter to an outlet in the side of the digester.

FIGS. 6E-6G depict several additional embodiments of the present invention wherein an auger assembly 60 is included inside the vessel 12. In the embodiments depicted in FIGS. 6E-6G, outlet 38 is positioned in the bottom 36 of digester 10. In the depicted embodiments, the auger assembly 60 includes a plurality of flights 64a and 64b that are oppositely angled so as to carry accumulated material from the sides of digester 10 toward outlet 38 in the middle. FIG. 6G depicts an embodiment that is similar to FIG. 6D in which digester 10 is equipped with a trough-shaped bottom.

Figure 6H:
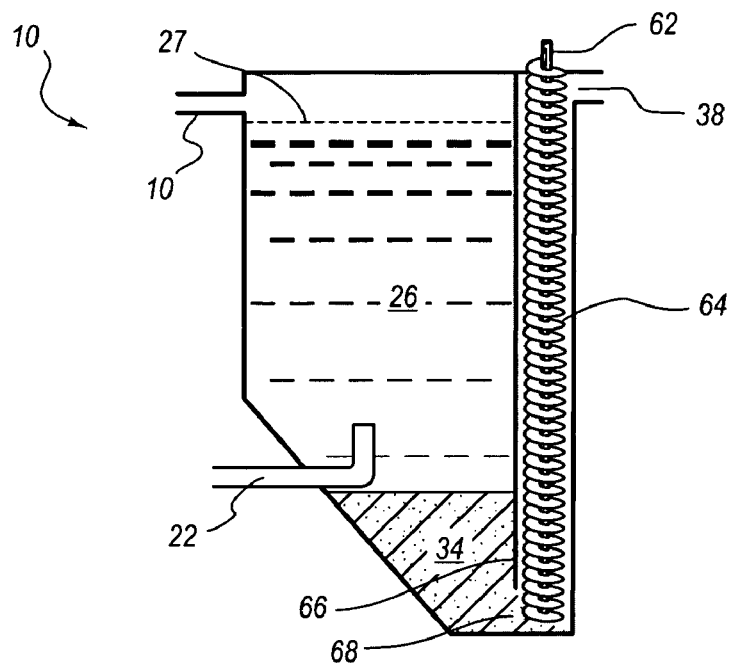
FIG. 6H illustrates a digester having a auger extends from the bottom of the digester above the liquid level.

FIG. 6H depicts another alternative embodiment of the present invention in which a digester 10 with a cone-shaped bottom is equipped with an auger assembly 60 that is configured so as to carry material from the bottom of the cone up to an outlet 38 positioned on the side of digester 10. In the depicted embodiment, outlet 38 is positioned on the lower portion of digester 10. In an alternative embodiment, the outlet could be positioned higher up on digester 10 where it would be above the liquid level.

The auger assembly 60 depicted in FIG. 6H includes a shaft 62, a plurality of flights 64 that carry accumulated matter toward outlet 38, and a housing 66 that partially encloses the plurality of flights 64.

It is often the case that the flushed solid, non-digestible 34 matter and the accompanying liquid contains undigested organic matter that can be put back into the digester 10. One embodiment of the present invention, therefore, includes methods whereby the flushed solid, non-digestible matter 34 is collected and the liquid portion is reinjected into the digester 10.

Figure 7:
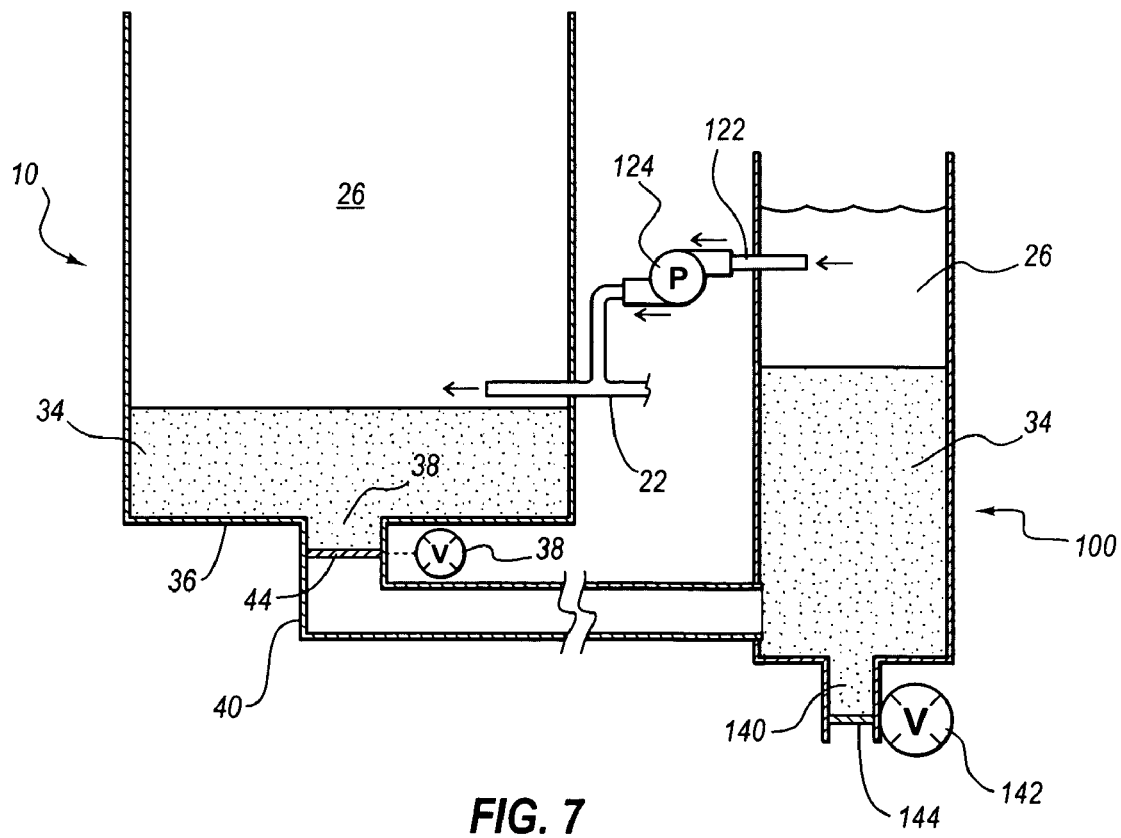
FIG. 7 a digester that is coupled to a clarifier tank for recycling liquid back into the digester.

FIG. 7 depicts one embodiment of a system for collecting and reinjecting the liquid portion. FIG. 7 shows a typical digester 10 that is coupled to a clarifier tank 100 for collecting and clarifying the flushed material 34 the digester. As in previous embodiments, the accumulated matter 34 is flushed from the digester 10 when valve 44 is opened with valve opener 42. The percent of the total volume of digester 10 that is removed when flushing the accumulated solids 34 is controlled so as to avoid interfering with the steady-state operation of digester 10.

In the embodiment depicted in FIG. 7, outlet pipe 40 is coupled to clarifier tank 100. The flushed material 34 includes solid, non-digestible matter and biomass 26. In the depicted embodiment, the solid, non-digestible matter 34 is allowed to settle in clarifier tank 100. After the solids 34 have settled, the liquid and biomass 26 is pumped back into digester 10 using pump 124 and liquid outlet 122 that are coupled to the liquid inlet 22 of digester 10. Accumulated solids can be flushed from clarifier tank 100 via outlet pipe 140, which includes valve 144 and valve opener 142.

While this invention has been described with reference to certain specific embodiments and examples, those skilled in the art will recognize that many variations are possible without departing from the scope and spirit of this invention. The invention, as defined by the claims, is intended to cover all changes and modifications of the invention which do not depart from the spirit of the invention. The words "including" and "having," as used in the specification, including the claims, shall have the same meaning as the word "comprising."

The present invention may be embodied in other specific forms without departing from its spirit or essential characteristics. The described embodiments are to be considered in all respects only as illustrative and not restrictive. In particular, elements of the depicted embodiment may be combined with elements of other depicted embodiments without departing from the spirit or essential characteristics of the present invention. The scope of the invention is, therefore, indicated by the appended claims rather than by the foregoing description. All changes which come within the meaning and range of equivalency of the claims are to be embraced within their scope.

What is claimed is:

1. A method for continuous, steady-state operation of an anaerobic reactor for digesting biodegradable matter containing an amount of solid, non-digestible matter, the method comprising:

provide an upflow anaerobic digester for anaerobically digesting biodegradable matter using a bacterial culture, the upflow anaerobic digester comprising:

a vessel having a volume with a top that defines an upper portion of the vessel and a bottom that defines a lower portion of the vessel, a septum positioned within the vessel for maintaining the bacterial culture in the lower portion of the vessel, an aperture formed in the septum for allowing digested biodegradable matter and liquid to flow from the lower portion of the vessel to the upper portion of the vessel, an inlet coupled to the vessel for introducing biodegradable matter into the lower portion of the vessel, a gas port coupled to the upper portion of the vessel for collecting gasses produced in the vessel, a first outlet coupled to the upper portion of the vessel for directing digested biodegradable matter to the outside of the vessel, and a second outlet coupled to the bottom of the vessel for removing accumulated solid, non-digestible matter from the vessel;

providing a bacterial culture comprising a sludge layer in the lower portion of the vessel;

introducing an influent into the lower portion of the vessel, wherein the influent comprises a biodegradable component, a liquid component, and an amount of solid non-digestible matter;

operating the upflow anaerobic digester in a steady-state, wherein the biodegradable component is continuously available to the bacterial culture as a food source;

accumulating the solid, non-digestible matter below the sludge layer in the bottom of the vessel; and flushing at least a portion of the accumulated solid, non-digestible matter from the upflow anaerobic digester through the second outlet as a slurry that includes a liquid component, wherein the portion of the accumulated solid, non-digestible matter removed as a slurry does not exceed 30% of the volume of the vessel, so as to maintain the upflow anaerobic digester in the steady-state.

2. A method as in claim 1, wherein the portion of the accumulated solid, non-digestible matter removed as a slurry does not exceed 20% of the volume of the vessel, so as to maintain the upflow anaerobic digester in the steady-state.

3. A method as in claim 1, wherein the portion of the accumulated solid, non-digestible matter removed as a slurry does not exceed 10% of the volume of the vessel, so as to maintain the upflow anaerobic digester in the steady-state.

4. A method as in claim 1, wherein the portion of the accumulated solid, non-digestible matter removed as a slurry does not exceed 5% of the volume of the vessel, so as to maintain the upflow anaerobic digester in the steady-state.

5. A method as in claim 1, wherein the influent comprises animal and/or human excrement.

6. A method as in claim 1, wherein the non-digestible matter comprises is sand, sawdust, hair, straw, or combinations thereof.

7. A method as in claim 1, further comprising monitoring the influent to determine the amount of solid non-digestible matter contained in the organic waste matter.

8. A method as in claim 1, the upflow anaerobic digester further comprising an auger device operatively coupled to the vessel and positioned within the aperture so as to prevent clogging of the aperture.

9. A method as in claim 1, wherein the vessel further comprises a substantially non-planar bottom for facilitating removal of the accumulated non-digestible matter at the bottom of the vessel.

10. A method as in claim 1, the upflow anaerobic digester further comprising an auger device operatively coupled to the vessel and positioned within the second outlet so as to facilitate removal of the slurry and prevent clogging of the second outlet.

11. A method as in claim 1, the method further comprising:
collecting the flushed solid, non-digestible matter and the liquid component in a clarifier tank;
separating the liquid component from the solid component; and
recycling the liquid from the clarifier tank back into the upflow anaerobic digester.

12. A method as in claim 11, wherein the accumulated solid, non-digestible matter and the liquid component comprise undigested waste matter.

13. A method as in claim 11, wherein the clarifier tank further comprises:
at least one inlet coupled to the clarifier tank for introducing the flushed solid, non-digestible matter and the liquid into the clarifier tank;
at least one outlet for withdrawing liquid from the clarifier tank; and a pump coupled to the clarifier tank and the inlet of the upflow anaerobic digester for pumping liquid from the clarifier tank into the upflow anaerobic digester.

14. A method for continuous, steady-state production of methane using an upflow anaerobic digester for digesting biodegradable matter containing solid, non-digestible matter, the method comprising:
providing an upflow anaerobic digester for anaerobically digesting biodegradable matter using a bacterial culture, the upflow anaerobic digester comprising:
a vessel having a volume with a top and a bottom,
a septum positioned within the vessel so as to define an upper portion of the vessel and a lower portion of the vessel, the septum being configured so as to maintain the bacterial culture in the lower portion of the vessel,
an aperture formed in the septum for allowing digested biodegradable matter and liquid to flow from the lower portion of the vessel to the upper portion of the vessel,
an inlet coupled to the vessel for introducing biodegradable matter into the lower portion of the vessel,
a gas port coupled to the upper portion of the vessel for collecting gasses produced in the vessel,
a first outlet coupled to the upper portion of the vessel that defines a fluid level in the vessel, the first outlet directing digested biodegradable matter to the outside of the vessel, and
a second outlet coupled to the bottom of the vessel;
providing a bacterial culture comprising anaerobic bacteria for digesting the biodegradable matter, wherein the bacterial culture and ant least a portion of the biodegradable matter comprise a sludge layer in the lower portion of the vessel;
introducing an influent into the lower portion of the vessel, wherein the influent comprises a biodegradable component, a liquid component, and an amount of solid non-digestible matter;
operating the upflow anaerobic digester in a steady-state, wherein the biodegradable component is continuously converted to methane gas by the bacterial culture;
accumulating the solid, non-digestible matter below the sludge layer in the bottom of the vessel;
fluidizing the accumulated solid, non-digestible matter using a fluid injection system, the fluid injection system being situated toward the bottom of the vessel; and
removing a portion of the fluidized solid, non-digestible matter from the upflow anaerobic digester through the second outlet, wherein the portion of the fluidized solid, non-digestible matter removed does not exceed 30% of the volume of the vessel, so as to maintain steady-state methane production.

15. A method as in claim 14, the fluidizing further comprising:
supplying a flow of a liquid to the to the fluid injection system; and
injecting liquid jets from the fluid injection system into the solid, non-digestible matter so as to form a slurry.

16. A method as in claim 15, wherein the liquid comprises liquid effluent that is withdrawn from the upper portion of the vessel.

17. A method as in claim 15, wherein the liquid comprises water that is pumped into the vessel.

18. A method as in claim 14, wherein the fluid injection system comprises a sparger assembly comprised of a plurality of sparger arms contained inside the vessel substantially below the fluid level with each of the plurality of sparger arms having a plurality of sparger tubes, with the sparger tubes being configured to inject liquid into the accumulated, solid non-digestible matter so as to form a slurry.

19. A method as in claim 14, wherein the fluid injection system comprises a plurality fluid injection ports operably coupled to the vessel, with the plurality of fluid injection ports being configured to inject liquid into the accumulated, solid non-digestible matter so as to form a slurry.

20. A method as in claim 19, wherein the fluid injection ports are operably anglable so as to allow a flow of fluid to be directed into the accumulated, solid non-digestible matter.

21. A method as in claim 14, the upflow anaerobic digester further comprising an auger device operatively coupled to the vessel and positioned within the aperture so as to prevent clogging of the aperture.

22. A method as in claim 14, wherein the vessel further comprises a substantially non-planar bottom for facilitating removal of the fluidized solid, non-digestible matter.

23. A method as in claim 14, the upflow anaerobic digester further comprising an auger device operatively coupled to the vessel and positioned within the second outlet so as to facilitate removal of the slurry and prevent clogging of the second outlet.

24. A method for continuous, steady-state operation of an anaerobic reactor, the method comprising:
providing an upflow anaerobic digester for anaerobically digesting biodegradable matter using a bacterial culture, the upflow anaerobic digester comprising:
a vessel with a top and a bottom having a volume and a liquid level,
a septum positioned within the vessel so as to define an upper portion of the vessel and a lower portion of the vessel, the septum being configured so as to maintain the bacterial culture in the lower portion of the vessel,
an aperture formed in the septum for allowing digested biodegradable matter and liquid to flow from the lower portion of the vessel to the upper portion of the vessel,
an inlet coupled to the vessel for introducing biodegradable matter into the lower portion of the vessel,
a gas port coupled to the upper portion of the vessel for collecting gasses produced in the vessel,
a first outlet coupled to the upper portion of the vessel for directing digested biodegradable matter to the outside of the vessel,
a second outlet coupled to the bottom of the vessel, and
a first auger device operatively coupled to the vessel and positioned within the second outlet;
providing a bacterial culture comprising a sludge layer in the lower portion of the vessel;
introducing an influent into the lower portion of the vessel, wherein the influent comprises a biodegradable component, a liquid component, and an amount of solid non-digestible matter;
operating the upflow anaerobic digester in a steady-state, wherein the biodegradable component is continuously available to the bacterial culture as a food source;
accumulating the solid, non-digestible matter below the sludge layer in the bottom of the vessel;
flushing at least a portion of the accumulated solid, non-digestible matter from the upflow anaerobic digester through the second outlet;
rotating the auger device in the second outlet so as to facilitate removal of the solid, non-digestible matter and prevent clogging of the second outlet.

25. A method as in claim 24, wherein the portion of the accumulated solid, non-digestible matter removed as a slurry does not exceed 30% of the volume of the vessel, so as to maintain the upflow anaerobic digester in the steady-state.

26. A method as in claim 24, the upflow anaerobic digester further comprising a second auger device operatively coupled to the vessel and positioned within the aperture so as to prevent clogging of the aperture.

27. A method as in claim 24, the upflow anaerobic digester further comprising a substantially non-planar bottom with an outlet positioned for facilitating removal of the accumulated non-digestible matter at the bottom of the vessel.

28. A method as in claim 24, the first auger being configured so as to convey the accumulated non-digestible matter above the liquid level of the vessel so as to remove the solids from the digester with minimal removal of liquid.

* * * * *